US005783156A

United States Patent [19]

Renzi et al.

[11] Patent Number: 5,783,156

[45] Date of Patent: Jul. 21, 1998

[54] TRANSFER PORT SYSTEM BETWEEN STERILE ENVIRONMENTS

[75] Inventors: Ernesto Renzi, Youngstown, N.Y.; Johannes W. Krikhaar, Marum, Netherlands

[73] Assignee: The BOC Group, Inc., New Providence, N.J.

[21] Appl. No.: 682,250

[22] Filed: Jul. 17, 1996

Related U.S. Application Data

[63] Continuation-in-part of Ser. No. 401,390, Mar. 9, 1995, abandoned.

[51] Int. Cl.[6] .................... A61L 2/04; B01L 1/00; B01L 11/02

[52] U.S. Cl. .................... 422/292; 422/297; 422/300; 422/38; 312/1

[58] Field of Search .................... 422/125, 120, 422/307, 297, 300, 38; 312/1

[56] References Cited

U.S. PATENT DOCUMENTS

| | | | |
|---|---|---|---|
| 5,139,459 | 8/1992 | Takahashi et al. | 454/187 |
| 5,313,738 | 5/1994 | Thakur et al. | 49/394 |
| 5,314,668 | 5/1994 | Beimaier | 422/292 |
| 5,425,400 | 6/1995 | Szatmary | 141/98 |
| 5,447,699 | 9/1995 | Papciak et al. | 422/294 |
| 5,451,131 | 9/1995 | Hecht et al. | 414/217 |

FOREIGN PATENT DOCUMENTS

| | | |
|---|---|---|
| 0 450 700 A1 | 3/1991 | European Pat. Off. . |
| 0662373 | 1/1995 | European Pat. Off. . |
| 1146767 | 3/1969 | United Kingdom . |
| 2262786 | 6/1993 | United Kingdom . |

*Primary Examiner*—Stephen Walsh
*Assistant Examiner*—Claire M. Kaufman
*Attorney, Agent, or Firm*—David M. Rosenblum; Salvatore P. Pace

[57] ABSTRACT

A transfer port system between two sterile environments having docked and undocked positions which is made up of two door frames connected to the environments and two doors connected to the two door frames. When the sterile environments are in the docked position the door frames of the two doors are juxtaposed and in close physical contact with one another and when the two sterile environments are in the undocked position the two door frames are spaced apart from one another and the two doors seal the sterile environments. The two door frames and the doors have a potentially non-sterile peripheral juncture located at the juncture between the doors and door frames when the doors are in a closed position sealing the sterile environments when the sterile environments are in their docked position. In order to sterilize this non-sterile peripheral junction, one or both of the door frames is provided with internal channels for circulation of a heat transfer fluid to heat the two door frames and the two doors and thereby sterilize said juncture. A vacuum sealing gasket is provided to allow a vacuum to be pulled between the two doors to hold the two doors together when the sterile environments are in the docked position. The two doors are then rotated as a unit between a closed position sealing the two sterile environments and an opened position away from the two door frames permitting transport through the two door frames and between the sterile environments.

10 Claims, 5 Drawing Sheets

TRANSFER PORT SYSTEM BETWEEN STERILE ENVIRONMENTS

This application is a continuation-in-part of application Ser. No. 08/401,390 filed Mar. 9, 1995, now abandoned.

BACKGROUND OF THE INVENTION

The present invention relates to a transfer port system for transferring articles between two sterile environments that are adapted to be brought into close proximity to one another by a docking operation. More particularly, the present invention relates to such a transfer port system in which one or both of the sterile environments is also a vacuum environment such as a freeze drier and the other of the sterile environments is an isolation chamber surrounding a loading cart designed to dock with the freeze drier.

Many industrial processes require the maintenance of clean sterile conditions during product manufacture and packaging. This requirement is no where greater than in the pharmaceutical industry in which products are manufactured and packaged under predefined conditions of sterility in order to prevent bacterial contamination. In the packaging of pharmaceutical products, vials are washed and are then conveyed through a sterilizing tunnel to a filling machine which provides a sterile environment to fill the vials with product and to loosely cap the vials with stoppers. Afterward, the vials travel to a clean room where they are accumulated on an accumulation table. The vials are then loaded on a loading cart, a motorized vehicle designed to convey the vials to a portal of a freeze drier projecting into the clean room. The loading cart has a sliding table that projects into the freeze drier portal to allow the vials to be shifted to the freeze drier shelves. Each freeze drier shelf is raised into a loading position, loaded and raised to raise the next underlying shelf into the loading position. At the conclusion of the freeze drying operation a hydraulic ram within the freeze drier packs the stoppers into the vials.

As can be appreciated, the maintenance of a clean room is an expensive proposition. Moreover, the worker must be clothed in clean suits which are uncomfortable and require workers to leave the clean room for relaxation and relief. As will be discussed the present invention provides a transfer port system that is particularly suitable for use in providing a sterile interface between an accumulation table and a loading cart and also a sterile interface between the loading cart and a freeze drier in order to eliminate the clean room. It is to be noted, and as will become apparent, the present invention is not limited to freeze drying applications.

SUMMARY OF THE INVENTION

The present invention provides a transfer port system between two sterile environments having docked and undocked positions. The transfer port system is formed of two door frames connected to the two sterile environments and two doors connected to the two door frames so that when the two sterile environments are in their docked position, the two frames and the two doors are juxtaposed and in contact with one another. When the two sterile environments are in the undocked position, the two door frames are spaced apart from one another and the two doors seal the two sterile environments. The two door frames and doors have a potentially non-sterile peripheral juncture located at the outer periphery of the two doors when in their juxtaposition. A door connection means is provided for connecting the two doors to one another when the two sterile environments are in the docked position. The door connection means can have means for producing a vacuum between the two doors or an electromagnetic coupling between the two doors. An opening means is provided for opening the two doors. The opening means has means for moving the doors when connected to one another between a closed position sealing the two sterile environments and an open position away from the two door frames permitting transport through the two door frames and between the two sterile environments. Heating means are provided for heating and thereby sterilizing said potentially non-sterile peripheral juncture. Such heating means can comprise at least one of the two door frames having internal channels for circulation of the heat transfer fluid to heat the two door frames and the two doors and thereby to sterilize the potentially non-sterile peripheral juncture. An inlet and an outlet to the internal channels are provided for introducing the heat transfer fluid into the internal peripheral channels and for discharging the heat transfer fluid from the internal channels, respectively.

The use of the heat transfer fluid permits temperatures within the potentially nonsterile peripheral juncture to be maintained in a range of between about 150° C. and about 300° C. for long periods of time. This will guarantee terminal sterilization. In an application of the present invention involving freeze dryers, the heat transfer fluid can be formed from diathermic fluid that is being used to heat freeze dryer shelves during the freeze dryer process. Hence, the transfer port of the present invention although not limited to applications involving the use of freeze dryers can be very advantageously utilized in connection with pharmaceutical manufacturing employing freeze dryers in the preparation and packaging of product.

BRIEF DESCRIPTION OF THE DRAWINGS

While the specification concludes with claims distinctly pointing out the subject matter that Applicant's regard as their invention, it is believed that the invention will be better understood when taken in connection with the accompanying drawings in which:

DETAILED DESCRIPTION

Figure 1:
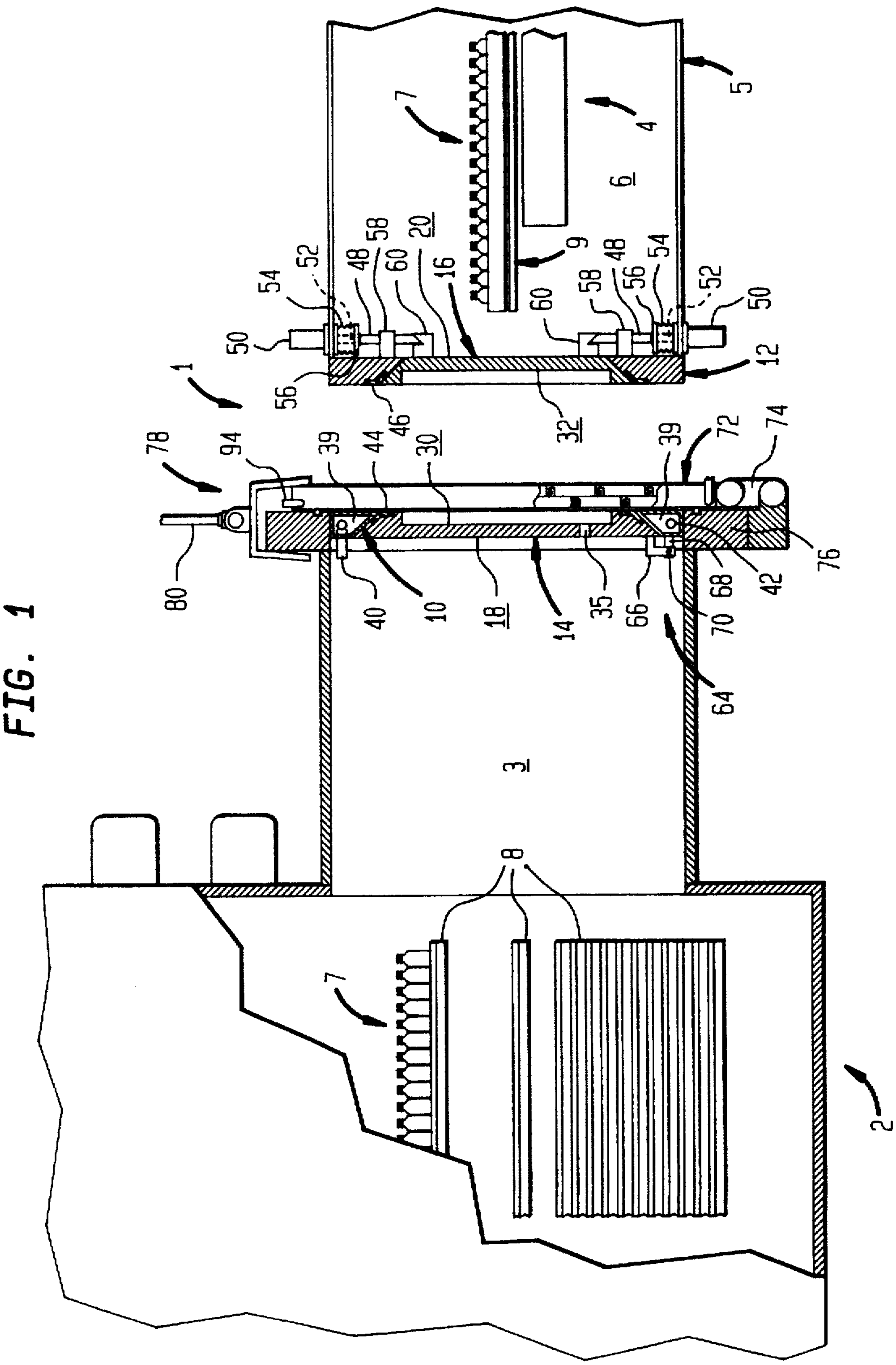
FIG. 1 is a fragmentary, cross-sectional view of a freeze drier and loading cart employing a docking port system in accordance with the present invention. In this illustration, the sterile environments of the freeze dryer and the loading cart are shown in their undocked position.
Figure 2:
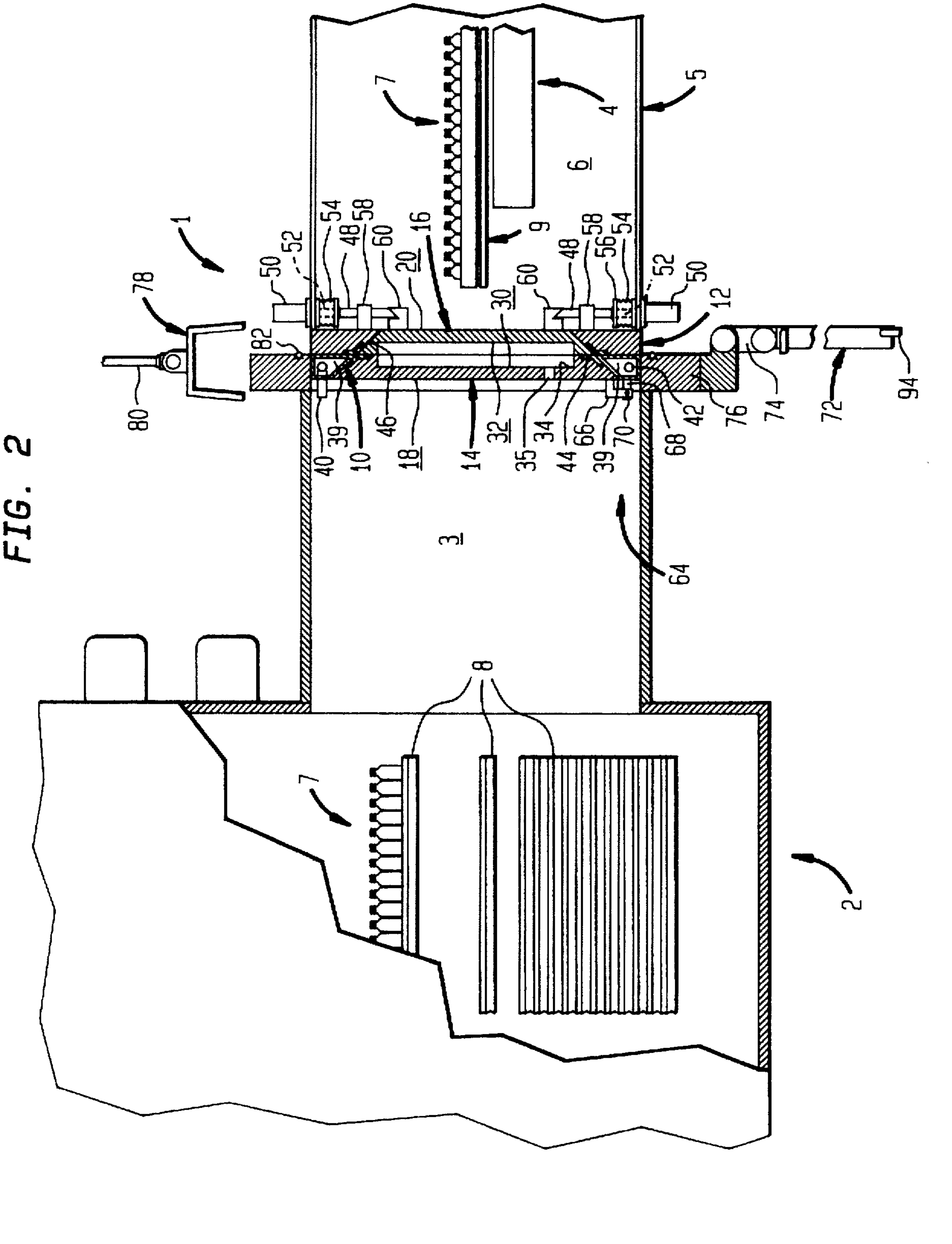
FIG. 2 is a fragmentary, cross-sectional view of the freeze drier and loading cart shown in FIG. 1 in the docked position.

With reference to FIG. 1, a transfer port system 1 in accordance with the present invention is illustrated as being applied to a freeze dryer 2 having an internal sterile environment 3 and loading cart 4. Loading cart 4 is surrounded by an isolation chamber 5 to provide a sterile environment 6. The base structure of loading cart 4, also not illustrated, would project through isolation chamber 5 and would be sealed at the locations at which isolation chamber 5 were penetrated by such base structure so as to maintain sterile environment 6. With additional reference to FIG. 2, loading cart 4 is a conventional loading cart and is designed so that sterile environment 6 can assume the docked position with internal sterile environment 3 of freeze drier 2. As illustrated, loading cart 4 holds trays of vials 7 to be loaded onto freeze dryer shelves 8 on an extensible or sliding table portion 9. Table portion 9 is designed to extend into freeze drier 2 to accomplish the loading in a known manner.

Vials 7 are retrieved from an accumulation table having an isolated environment and a door system, which although not shown, would include an isolated environment such as the type of environment provided by isolation chamber 5 and a door system sharing similar components to those used in connection with freeze drier 2. The environment used with the accumulation table allows transfer of vials 7 from the sterile environment of the accumulation table to the sterile environment provided by isolation chamber 5 of loading cart 4 under predetermined sterile conditions. Thereafter, vials 7 are again transferred from loading cart 4 and isolation chamber 5 to internal sterile environment 3 of freeze dryer 2, again, under such predetermined sterile conditions. As such, there is no need for a clean room to be provided for loading cart 4 to travel between the accumulation table and freeze drier 2.

It is to be noted that although transfer port system 1 of the present invention is illustrated with respect to a freeze dryer, the invention is not intended to be limited to freeze drying applications. The invention would have applicability to any transfer port need were there is a requirement of between environments under sterile conditions.

Transfer port system 1 is provided with two door frames 10 and 12 which are respectively connected to freeze dryer 2 and isolation chamber 5. Two doors 14 and 16 are connected to door frames 10 and 12 so that when in the docked position, door frames 10 and 12 and doors 14 and 16 are in the illustrated juxtaposed position, in close physical contact with one another. In the undocked position, door frames 10 and 12 and therefore, doors 14 and 16 are spaced apart from one another with doors 14 and 16 respectively sealing sterile environments 3 and 6. Door frames 10 and 12 and doors 14 and 16 are substantially of rectangular configuration with doors 14 and 16 having rounded corners.

Figure 3:
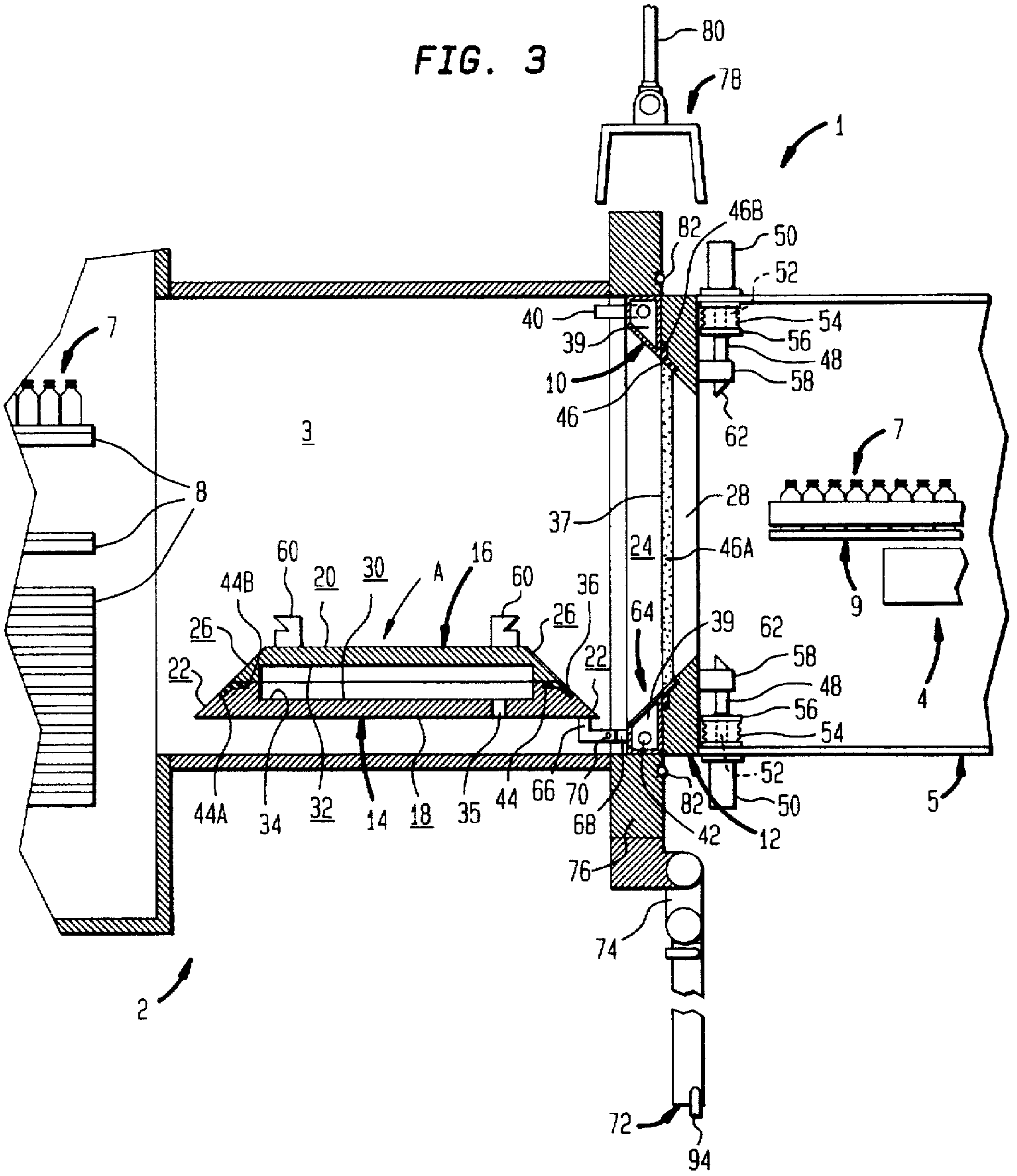
FIG. 3 is a fragmentary, cross-sectional view of the freeze drier and loading cart in the docked position shown in FIGS. 2 and with doors in an open position to allow transfer of articles through the transfer port.

With reference to FIG. 3, surface 18 of door 14 and surface 20 of door 16 are sterile surfaces because they are located within sterile environments 3 and 6, respectively. Additionally, peripheral surfaces 22 and 24 of door 14 and door fame 10, respectively, and peripheral surfaces 26 and 28 of door 16 and door frame 12, respectively, are sterile surfaces as well. The juxtaposed surfaces of doors 14 and 16 are provided with central recessed surfaces 30 and 32 to form a chamber 34 having a vacuum inlet 35 which will be discussed hereinafter. These aforementioned surfaces, although not sterile, are in close physical contact when sterile environments 3 and 6 are in the docked position. However, an outer juncture 36 between doors 14 and 16 and an inner juncture 37 of door frames 10 and 12 is not sterile. As will discussed, doors 14 and 16 are rotated in an opened position to open transfer port formed by door frames 10 and 12 and doors 14 and 16. Thus, a peripheral band A1 at door frames 10 and 12 and doors 14 and 16 is formed that is potentially not sterile.

In order to sterilize this peripheral band of non-sterility, peripheral channels 39 are provided for circulating a heat transfer fluid in door frame 10. Since door frame 10 is of rectangular configuration, horizontal segments of peripheral channels 39 which are illustrated in cross-section in FIGS. 1 and 2 would communicate with vertical segments of peripheral channels 39. The transfer fluid enters peripheral channels 39 through a fluid inlet 40 and is discharged from peripheral channels 39 via a fluid outlet 42. As could be appreciated, peripheral channels 39 could be provided in door frame 12 but not in door frame 10 or alternatively, peripheral channels such as peripheral channels 39 could be provided in both door frames 10 and 12. Also, peripheral channels could be provided within either or both of doors 14 and 16. It should also be pointed out that the sterile isolation chamber of the accumulation table (described herein but not illustrated) would have a door and door fame combination that would be the same as that illustrated for door frame 10 and door 14 thereof. A source of heat transfer fluid would be provided for sterilization purposes mentioned above. In place of the foregoing heating by heat transfer fluid, electrical, cartridge-type heaters could be located within one or both door frames 10 and 12.

When sterile environments 3 and 6 are is the docked position, a connection means is provided for connecting doors 14 and 16 to one another. Since the freeze drying process involves the sublimation of water under subatmospheric conditions, a source of vacuum is provided which is applied to chamber 34 through vacuum inlet 35. Although not shown, a vacuum line would lead to the vacuum supply of freeze dryer 2. In order to draw a vacuum in chamber 34, a peripheral vacuum sealing gasket 44 is provided for door 14 and a similar peripheral vacuum sealing gasket 46 is provided for door frame 12. The application of vacuums holds doors 14 and 16 tightly against one another so that they can be rotated as a unit into an open position allowing transfer of vials 8 through door frames 10 and 12 and thus, transfer port system 1. In a proper application of the present invention, a mechanical latching mechanism or an electromagnetic latching mechanism could be used in place of the vacuum system, described above, to hold doors against one another. In this regard, the electromagnetic latching mechanism could comprise electromagnets recessed in one of doors 14 and 16 and complementary ferromagnetic materials recessed within the other of the doors 14 and 16 (if doors are made from a weak or non-ferromagnetic material) to be attracted by the electromagnets and thus hold the doors together.

Peripheral vacuum sealing gasket 44 has adjacent sealing surfaces 44A and 44B set within peripheral surfaces 22 and of door 14 and the front surface portions of door 14 to seal against the peripheral surfaces of door frame 10 and the front surface portions of door 16. Similarly peripheral vacuum sealing gasket 46 has sealing surfaces 46A and 46B set within peripheral surfaces 28 of door frame 12 and the front surface portions thereof to seal against the peripheral surfaces 26 of door 16 and the front surface portions of door frame 12. In cross-section, peripheral sealing gaskets 44 and 46 have an arrowhead-like configuration. Their point of contact defines peripheral band 38 of non-sterility that must be sterilized in order to ensure and maintain sterile conditions within transfer port system 1. Vacuum sealing gaskets 44 and 46 would be molded in position to prevent separation from doors 14 and 16 and discontinuous backing on doors 14 and 16.

Door 16 is held in place and released from door frame 12 by means that can comprise a system of latching pins 48 which are activated by a double acting solenoid 50 having an actuating arm 52 acting within a welded steel bellows 54. Actuating arm 52 acts against a crown piece 56 that is connected to bellows 54 and actuating arm 52. Latching pin 48 is in turn connected to crown piece 56 such as by welding. A guide 58 is provided to guide latching pin 48 into a latch member 60 connected to door 16. It is to be noted that both latch member 60 and a distal end 62 of latching pin 48 are wedge shaped. The angles of these wedges are not equal so that when distal end 62 of latching pin 48 is seated within latching member 60, door 16 is driven inwardly of door frame 12 to produce a hermetic seal.

Door 14 is held in position by a motorized hinge mechanism 64 which has a pivoting L-shaped lug 66 connected to door 14 and a stationary lug 68 connected to door frame 10. Two or more set of such hinge mechanisms would be used to support door 14 in both the closed and open positions thereof and for pivoting door 14 between such positions. A motor driven shaft 70 rotates within stationary lug 68 and is further attached to pivotable L-shaped lug 66 to move door 14 between closed and open positions.

When sterile environments 3 and 6 are in the docked position, a vacuum is drawn within chamber 34 causing doors 14 and 16 to be held tightly against one another. At the same time solenoids 50 are activated to move latching pins 48 outwardly so that distal end 62 of pins 48 unseat from latching members 60. Thereafter, motor driven shaft 70 rotates in a counterclockwise direction of rotation pivoting doors 14 and 16 in a counterclockwise and downward direction indicated by arrowhead A to open the transfer port and to allow transfer of vials 7 onto shelves 8.

Figure 4:
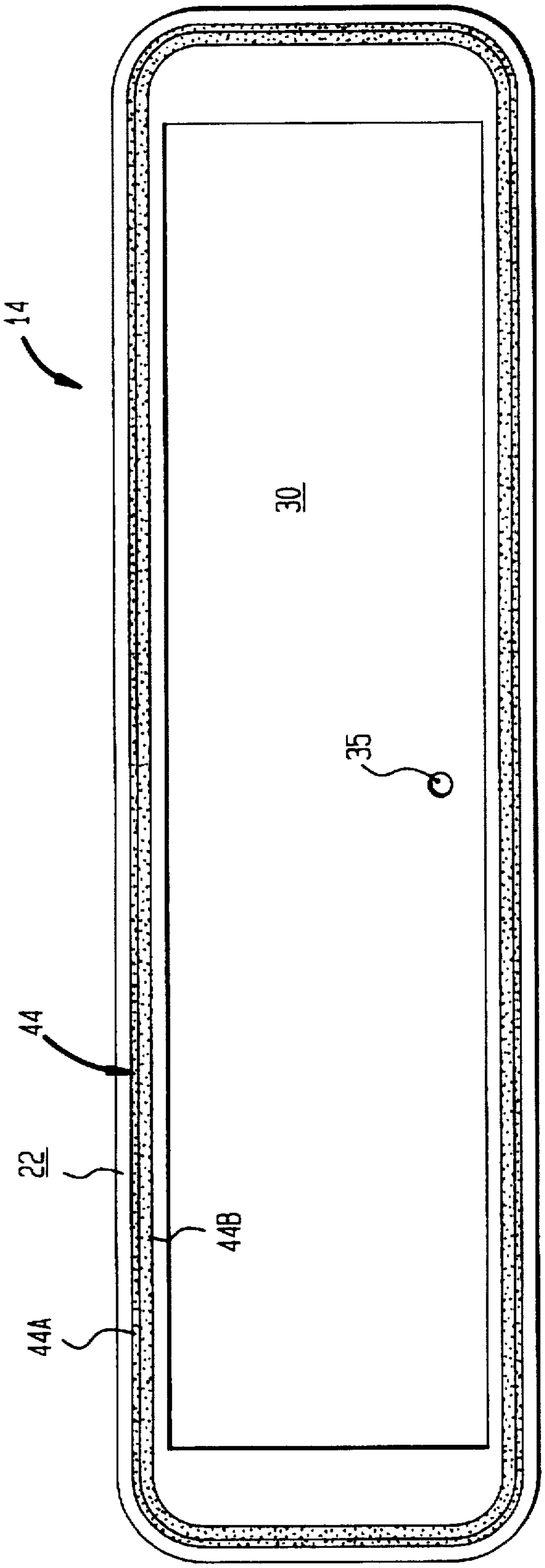
FIG. 4 is a front elevational view of a door used in the transfer port system of the present invention.

With further reference now to FIG. 4, it is to be noted that when sterile environments 3 and 6 are in the docked position and a vacuum is drawn forcing doors 14 and 16 against one another a solid object is formed having the shape of a frustum of a pyramid. In fact, each door is so shaped. In this regard, the shorter traverse sides of each of doors 14 and 16 are angled in the manner of the longer sides shown in section in the illustrations herein. This shape is not exactly a pyramid in that the corners are rounded to permit use of peripheral vacuum sealing gaskets 44 and 46. The pyramid-like shape is necessary so that doors 14 and 16 can be given a rectangular configuration while being allowed pivotable motion out of door frames 10 and 12. For instance, if the peripheral sealing surfaces of doors 14 and 16 were not angled as illustrated, the assemblage of doors 14 and 16 could not be rotated out of door frames 10 and 12.

Figure 5:
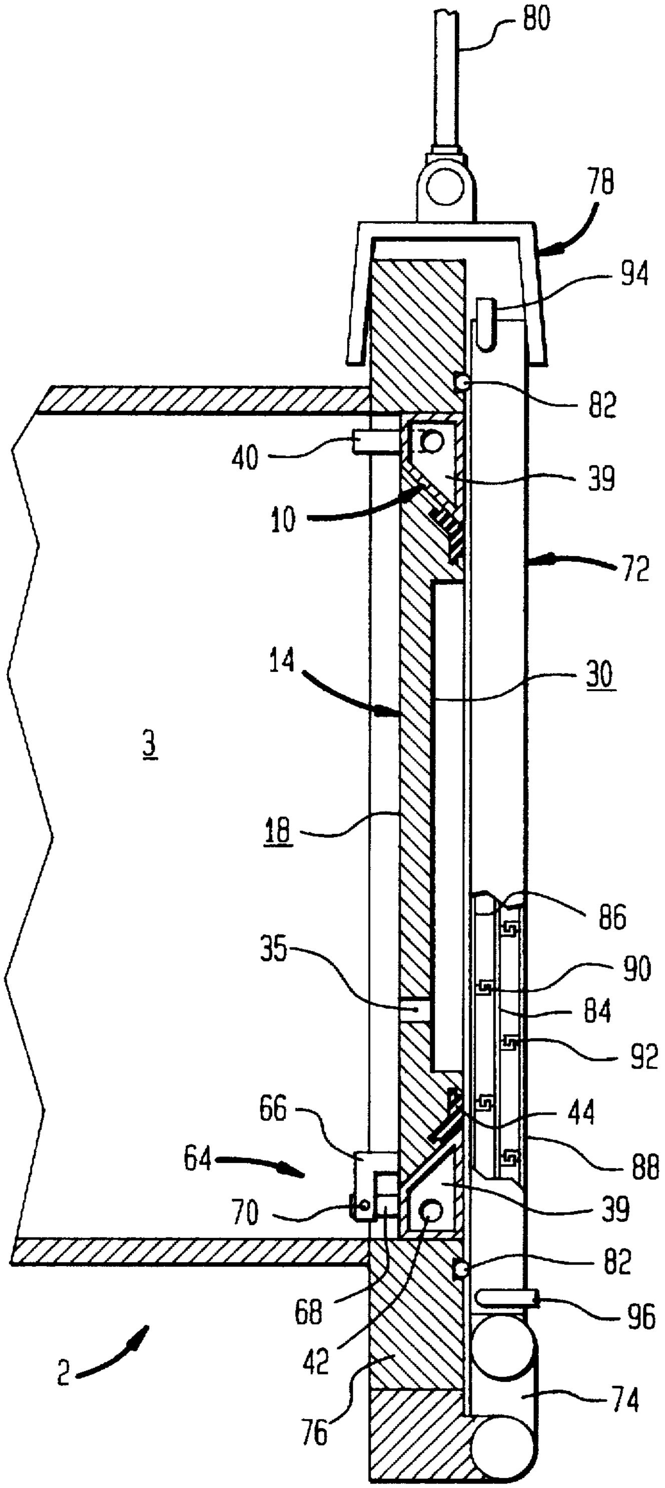
FIG. 5 is an enlarged fragmentary view of FIG. 1 illustrating an outer vacuum door in accordance with the present invention.

Referring to FIG. 5, where one of these sterile environments is also a vacuum environment such as in a freeze dryer, an outer vacuum door 72 can be utilized. Vacuum door 72 is hinged by hinge mechanism 74 to an outer frame-like member 76 and is latched in place against outer frame-like member 76 via a latching mechanism 78 which is activated via a hydraulic actuator, only the actuating rod 80 of which is illustrated in the figures. Frame-like member 76 is provided with a vacuum 0 ring sealing gasket 82 that surrounds door frame 10 to produce a vacuum seal surrounding door frame 10 and door 14.

Vacuum door 72 has a layered construction formed by central plate 84 and opposed inner and outer plates 86 and 88. A plurality of ribs 90 separate inner plate 86 from central plate 84 and the plurality of ribs 92 separate outer plate 88 from central plate 84. The aforementioned ribs and plates are constructed with the ribs having an interlocking construction of two elements which can be separately welded to the plates and then interlocked during final assembly. Ribs 90 are staggered in a direction normal to the illustration so that an inner layer of vacuum door 72 can act as a heat exchanger to circulate diathermic fluid (or other heat transfer fluid in case of other applications of transfer port system 1) through the inner layer of vacuum door 72. To this end, the formed heat exchanger has an inlet 94 and an outlet 96. The outer layer formed between outer plates 88 and central plate 84 is vacuum sealed to provide vacuum insulation and protection of workmen passing transfer port system 1 when loading cart 4 and therefore the sterile environments 3 and 6 are in the undocked position. Again ribs 92 can be staggered in a direction normal to the illustration for this purpose.

While the present invention has been described with reference to a preferred embodiment, it will occur to those skilled in the art that numerous changes, additions and omissions may be made without departing from the spirit and scope of the present invention.

What is claimed is:

1. A transfer port system between two sterile environments having docked and undocked positions, said transfer port comprising;

two door frames connected to said two sterile environments and two doors connected to said two door frames so that when said two sterile environments are in said docked position, said two door frames and said two doors are juxtaposed and in contact with one another and when said two sterile environments are in said undocked position, said two door frames are spaced apart from one another and said two doors seal said two sterile environments;

said two door frames and doors having a potentially non-sterile peripheral juncture located at an outer periphery of the two doors when in their said juxtaposition;

door connection means for connecting said two doors to one another when said two sterile environments are in the docked position; and opening means for opening said two doors, said opening means having means for moving said doors when connected to one another between a closed position sealing said two sterile environments and an open position away from said two door frames permitting transport through said two door frames and between said two sterile environments;

at least one of said two door frames having internal channels for circulation of a heat transfer fluid to heat the two door frames and said two doors and thereby sterilize said potentially non-sterile peripheral juncture, an inlet and an outlet to said internal channels for introducing said heat transfer fluid into said internal channels and for discharging said heat transfer fluid from said internal channels, respectively.

2. A transfer port system between two sterile environments having docked and undocked positions, said transfer port system comprising:

two door frames connected to said two sterile environments and two doors connected to said two door frames so that when said two sterile environments are in said docked position, said two door frames and said two doors are juxtaposed and in contact with one another and when said two sterile environments are in said undocked position, said two door frames are spaced apart from one another and said two doors seal said two sterile environments;

said two door frames and doors having a potentially non-sterile peripheral juncture located at an outer periphery of the two doors when in their said juxtaposition;

door connection means having means for producing a vacuum between said two doors or an electromagnetic coupling between said two doors for connecting said two doors to one another when said two sterile environments are in the docked position;

opening means for opening said two doors, said opening means having means for moving said doors when connected to one another between a closed position sealing said two sterile environments and an open position away from said two door frames permitting transport trough said two door frames and between said two sterile environments; and heating means for heating and thereby sterilizing said potentially non-sterile peripheral juncture.

3. The transfer port system of claim 2, wherein said heating means comprises at least one of said two door frames having internal channels for circulation of a heat transfer fluid to heat the two door frames and said two doors and thereby sterilize said potentially nonsterile peripheral juncture, an inlet and an outlet to said internal channels for introducing said heat transfer fluid into said internal peripheral channels and for discharging said heat transfer fluid from said internal peripheral channels, respectively.

4. The transfer port system of claim 1, wherein said door connection means comprises: said two doors having central recessed surfaces forming a chamber between said two doors during said docked position of said two sterile environments;

vacuum sealing means surrounding said chamber for forming a vacuum seal between said two doors; and an inlet to said chamber for subjecting said chamber to a subatmospheric pressure, thereby to connect said two doors to one another during said docked position of said two sterile environments.

5. The transfer port system of claim 1 or claim 2 or claim 3, wherein:

said two doors are of rectangular configuration and have peripheral edges shaped so that said two doors when connected to one another form a frustum of a pyramid; and said opening means include pivotable connection means for pivotably connecting one of said two doors forming a base of said frustum to one of said two frames.

6. The transfer port system of claim 5, further comprising connection means for releasably connecting one of said two doors to one of said two door frames so that when said two doors are connected said one of said two doors releases from said one of said two door frames and when said two sterile environments are in their said undocked positions, said one of said two doors is connected to said one of said two door frames.

7. The transfer port system of claim 2, wherein:

at least one of said two sterile environments is also a vacuum environment; and said transfer port system further comprises at least one outer vacuum door hinged to at least one of said two door frames and sealing means for sealing said at least one outer vacuum door to said at least one of said two door frames.

8. The transfer port system of claim 7, wherein said sealing means comprises a vacuum O-ring seal set within said at least one of said two door frames.

9. The transfer port system of claim 8, wherein said at least one vacuum door has an inner layer configured to act as a heat exchanger for circulating said heat exchange fluid therewithin and an outer vacuum sealed layer, adjacent said inner layer.

10. The transfer port system of claim 9, wherein: said two doors are of rectangular configuration and have peripheral edges shaped so that said two doors when connected to one another form a frustum of a pyramid; said opening means include pivotable connection means for pivotably connecting one of said two doors forming a base of said frustum to one of said two frames, and said transfer port further comprises releasable connection means for releasable connecting the other of said two doors to the other of said two door frames so that when said two doors are connected said other of said two doors releases from said other of said two door frames and when said two sterile environments are in their said undocked positions, said other of said two doors is connected to said other of said two door frames.

* * * * *